US006706267B1

(12) United States Patent
Adalsteinsson et al.

(10) Patent No.: US 6,706,267 B1
(45) Date of Patent: Mar. 16, 2004

(54) GLUCOSAMINE AND EGG FOR REDUCING INFLAMMATION

(75) Inventors: Orn Adalsteinsson, Kennett Square, PA (US); Jeffrey G. Hunchar, West Chester, PA (US); Subramanian Iyer, Hockessin, DE (US)

(73) Assignee: Arkion Life Sciences LLC, Wilmington, DE (US)

( * ) Notice: Subject to any disclaimer, the term of this patent is extended or adjusted under 35 U.S.C. 154(b) by 195 days.

(21) Appl. No.: 09/656,712

(22) Filed: Sep. 7, 2000

Related U.S. Application Data
(60) Provisional application No. 60/153,887, filed on Sep. 14, 1999, and provisional application No. 60/192,386, filed on Mar. 27, 2000.

(51) Int. Cl.[7] .................... A61K 39/395; C07K 1/00
(52) U.S. Cl. ................ 424/157.1; 424/130.1; 530/395; 530/300; 530/350; 435/4
(58) Field of Search .......... 424/130.1, 157.1; 530/395, 300, 350; 435/4

(56) References Cited

U.S. PATENT DOCUMENTS

| | | | | |
|---|---|---|---|---|
| 4,357,272 A | | 11/1982 | Polson .................. 260/112 R |
| 4,367,309 A | * | 1/1983 | Kondo et al. ............... 525/54.1 |
| 4,473,551 A | * | 9/1984 | Schinitsky ................... 424/95 |
| 4,550,019 A | | 10/1985 | Polson ....................... 424/85 |
| 4,748,018 A | | 5/1988 | Stolle et al. .................. 424/87 |
| 5,772,999 A | | 6/1998 | Greenblatt et al. ....... 424/187.1 |
| 6,162,787 A | * | 12/2000 | Sorgente et al. ............... 514/2 |
| 6,251,863 B1 | * | 6/2001 | Yue .............................. 514/12 |
| 6,451,771 B1 | * | 9/2002 | Henderson et al. .......... 514/54 |

FOREIGN PATENT DOCUMENTS

| | | |
|---|---|---|
| WO | WO 97/35595 | 10/1997 |
| WO | WO 98/04273 | 2/1998 |
| WO | WO 99/36077 | 7/1999 |

OTHER PUBLICATIONS

CV–0083A—Specification.

* cited by examiner

*Primary Examiner*—James Housel
*Assistant Examiner*—Stacy B. Chen
(74) *Attorney, Agent, or Firm*—Basil S. Krikelis

(57) ABSTRACT

The invention is directed to a composition and method for the treatment and prevention of inflammation and inflammatory related disorders. The composition is glucosamine in combination with an egg product. It is generally preferred that the egg product is obtained from an avian which has been hyperimmunized with an immungenic mixture and/or which contains an anti-inflammatory composition.

12 Claims, 2 Drawing Sheets

GLUCOSAMINE AND EGG FOR REDUCING INFLAMMATION

RELATED APPLICATIONS

This application claims the benefit of U.S. Provisional Application No. 60/153,887, filed Sep. 14, 1999 and U.S. Provisional Application No. 60/192,386, filed Mar. 27, 2000.

BACKGROUND OF THE INVENTION

Field of the Invention

The invention relates to a method of reducing inflammation in animals. More particularly, the invention relates to the combination of egg product and glucosamine to produce a synergistic effect in reducing inflammation, and particularly arthritis, in animals.

Inflammation

Inflammation, as defined in Dorland's Medical Dictionary, is "a localized protective response, elicited by injury or destruction of tissues, which serves to destroy, dilute or wall off both the injurious agent and the injured tissue." It is characterized by fenestration of the microvasculature, leakage of the elements of blood into the interstitial spaces, and migration of leukocytes into the inflamed tissue. On a macroscopic level, this is usually accompanied by the familiar clinical signs of erythema, edema, hyperalgesia (tenderness), and pain.

During this complex response, chemical mediators such as histamine, 5-hydroxytryptamine, various chemotactic compositions, bradykinin, leukotrienes, and prostaglandins are liberated locally. Phagocytic cells migrate into the area, and cellular lysosomal membranes may be ruptured, releasing lytic enzymes. All of these events can contribute to the inflammatory response.

In the particular case of rheumatoid arthritis, the resulting inflammation likely involves the combination of an antigen with an antibody complement causing the local release of chemotactic and chemoactivating compositions that attract leukocytes. The leukocytes phagocytose the complexes of antigen-antibody and complement, and also release the many enzymes contained in their lysosomes. These lysosomal enzymes then cause injury to cartilage and other tissues, and this furthers the degree of inflammation. Cell-mediated immune reactions may also be involved. Prostaglandins, which are key intracellular regulators of cellular function, are also released during this process.

The inflammatory response is any response characterized by inflammation as defined above. It is well known, to those skilled in the medical arts, that the inflammatory response causes much of the physical discomfort (i.e., pain and loss of function) that has come to be associated with different diseases and injuries.

Arthritis

Arthritis manifests itself in a variety of forms. Some of the more common forms include rheumatoid arthritis, osteoarthritis and generalized rheumatism.

Rheumatoid arthritis is an autoimmune disease characterized by pain, swelling and stiffness in the joints. Rheumatoid arthritis is a disease which afflicts approximately 3% of Americans, and particularly women. Rheumatoid arthritis is an extremely disabling disease and usually strikes adults between the ages of 30 and 40 years, while the occurrence of clinical illness is greatest among those aged 40–60 years. Although drug therapy is somewhat effective, as many as 7% of rheumatoid arthritis sufferers are disabled to some extent as quickly as 5 years after disease onset, and within 10 years, as many as 50% are too disabled to work.

Osteoarthritis produces similar symptoms to rheumatoid arthritis. In particular, although osteoarthritis begins as a degeneration of particular cartilage whereas rheumatoid arthritis begins as inflammation in the synovium, each process approaches the other as the disease progresses. In osteoarthritis, as cartilage deteriorates and joint congruence is altered, a reactive synovitis often develops.

Conversely, as rheumatoid arthritis erodes cartilage, secondary osteoarthritis changes in bone and cartilage develop. At the end stages of both osteoarthritis and rheumatoid arthritis, the involved joints appear the same.

Some other forms of arthritis include Ankylosing Seronegative Spondyloarthropathy (ankylosing spondylitis) and reactive arthritis. These conditions are often referred to as the "B-27 associated diseases," and are difficult to differentiate from rheumatoid arthritis. In some cases ankylosing spondylitis, Reiters syndrome or psoriatic arthritis are present coincidingly with Rheumatoid Arthritis in the same patient. In many cases, these patients are treated with the same disease modifying drugs as those suffering from progressive rheumatoid arthritis.

Onset of arthritis generally occurs after the age of 30 in those who are susceptible to such disease. However, some forms of arthritis may be initiated by different causes, such as slow virus infections. Because there is great overlap, many physicians consider these forms as "generalized rheumatism" and approach management of the diseases in the same way. Some diseases which fall into this category include Chronic Fatigue Syndrome, fibromyalgia (fibrositis) and gout. In fact, for some patients, evidence is accumulating for superimposition of rheumatoid arthritis and fibromyalgia.

Autoimmune Diseases

As stated above, rheumatoid arthritis is an autoimmune disease, and as such, its etiology is much the same as the etiology of any other autoimmune disease. The body normally recognizes the difference between its own by-products and foreign invaders (i.e. bacteria, viruses, fungi and protozoans, to name a few). When an immune cell (T or B lymphocyte) reacts to a "self-protein" during its development, that cell is deemed defective and usually destroyed or inactivated. Sometimes, however, a "self-reactive" immune cell will escape destruction. At a certain later time, that cell can be activated and trigger an immune response. Activation is thought to occur after infection with a common bacteria or virus which contains a polypeptide having a stretch of amino acids which match a stretch on the defective self-protein. Several bacteria, such as Streptococcus, Mycoplasma, and borrelia, have been implicated in the initiation of the disease, as well as certain viruses, namely retroviruses. In addition to Rheumatoid Arthritis, autoimmunity often results in such diseases as juvenile diabetes, multiple sclerosis, Graves' disease, Meneri's disease, myasthenia gravis, lupus erythematosus and psoriasis. (Medical Sciences Bulletin, September, 1994).

Autoimmunity affects specific organs. For example, some autoimmune diseases of liver bile ducts, and kidneys are: primary biliary cirrhosis, necrotizing glomerulonephritis, "idiopathic" crescentic glomerulonephritis, virus-induced liver and kidney disease, chronic hepatitis, autoimmune and drug-induced hepatitis (Gershwin, Manns, and Mackay 1992). Immune destruction of the islets of Langerhans results in diabetes mellitus (Hagopian and Lerumark 1992) and insulin autoantibodies have been described (Palmer 1987).

There are a large category of systemic vasculitides diseases in which autoimmune mechanisms have been suggested as the cause of the pathogenesis. Some of the diseases are: leukocytoclastic angitis, polyarteritis nodosa, Goodpasture's syndrome, Kawasaki disease, Wegener's granulomatosis, Churg-Struass syndrome, giant-cell arteritis, Takayasu arteritis, immune-complex-mediated, lupus, rheumatoid, and cryoglobulinemic vasculitis, Henoch Schonlein purpura (Kallenberg, 1996; Jennette, Jones, Falk, 1992).

There is also a body of evidence that autoimmunity may play a role in many forms of heart disease including: postpericardiotomy and post myocardial infarction syndromes, myocarditis, and idiopathic dilated cardiomyopathy. Autoimmunity may be responsible for the progression of acute disease of heart muscle to degenerative (Rose, Neumann, Burek, Herskowitz 1992).

Symptomatic involvement of skeletal muscle is common in many autoimmune diseases such as polymyositis or inflammatory myopathy (which may include rheumatoid arthritis, polymyalgia rheumatica, myasthenia gravis, myasthenic myopathy, neurogenic atrophy, motor neuron disease, fibromyalgia, fibrositis, muscular dystrophy, endocrine, metabolic, and carcinomatous myopathy). (Hollingsworth, Dawkins, Thomas 1992).

Other diseases with autoimmune origins may be uveitis, Vogt-Koyanagi-Harada syndrome, (Detrick and Hooks 1992), and Sjögren's syndrome, scieroderma, ankylosing spondylitis, dermatomyositis, psoriasis, psoriatic arthritis, Reiter's syndrome (NIH 1994).

Also evidence of autoantibodies has been found in Alzheimer's disease (Singh et al., 1992), dementia complex (Mastroianni et al., 1991) and autistic children (Singhi et al., 1993).

Several neurologic diseases such as Sydenhar's Chorea, chronic obsessive-compulsive disorders (OCD), attention deficit hyperactivity disorder (ADHD), Tourette's Syndrome (TS) and some cases of schizophrenia may have an autoimmune component and may be associated with anti-neuronal antibodies (Medical Sciences Bulletin, September 1994).

This summary is not all inclusive and those in the art are familiar with other autoimmune diseases, such as, for example Guillain-Barrésyndrome (idiopathic polyneuritis).

Treatment

In order to treat inflammatory related disorders, it is a common medical practice to administer pharmacologic a l agents that reduce the physical discomfort of the inflammatory response. Agents having these properties are classified as anti-inflammatory. Anti-inflammatory drugs are used for the treatment of a wide spectrum of disorders , and the same drugs are often used to treat different diseases. Treatment with anti-inflammatory drugs is not for the disease, but most often for the symptom (i.e., inflammation).

The anti-inflammatory , analgesic, and anti-pyretic drugs are a heterogeneous group of compounds, often chemically unrelated, which nevertheless share certain therapeutic actions and side effects. Corticosteroids represent the most widely-used class of compounds for the treatment of inflammation. Proteolytic enzymes represent another class of compounds that are thought to have anti-inflammatory effects. Hormones that directly or indirectly cause the adrenal cortex to produce and secrete steroids represent another class of anti-inflammatory compounds. Unfortunately, the natural and synthetic corticosteroid preparations cause a number of severe side effects, including elevation of blood pressure, salt and water retention, kidney damage and increased potassium and calcium excretion. Moreover, corticosteroids may mask the signs of infection and enhance dissemination of infectious microorganisms. These hormones are considered unsafe for use in pregnant women, and long-term corticosteroid treatment has been associated with gastric hyperactivity and/or peptic ulcers. Treatment with corticosteroids may also aggravate diabetes mellitus, requiring higher doses of insulin, and may produce psychotic disorders. Hormonal anti-inflammatory agents which indirectly increase the production of endogenous corticosteroids have the same potential for adverse side-effects.

Another common treatment for inflammation, and in particular rheumatoid arthritis, other arthritis and other autoimmune diseases, is drug therapy. In general, patients are initially treated with "first-line" agents, usually non-steroidal anti-inflammatory drugs (NSAIDs) which primarily relieve the symptoms. The patients are later treated with "second-line" or disease-modifying agents (DMARDs) such as methotrexate, gold compounds, penicillamine, sulfasalazine, and antimalarial drugs. However, all of the above drugs have serious side effects, especially when administered in elevated doses. For example aspirin, an NSAID, may produce indigestion and stomach pain; phenylbutazone may produce stomach ulcers and phenacetin may lead to kidney disease. Methotrexate may cause oral ulceration and gastrointestinal (GI) side effects.

If a natural food product having anti-inflammatory effects could be obtained, it would provide an easily administratable, readily available, and safe therapeutic composition for the treatment of arthritis, autoimmune diseases and inflammation in general.

Passive Immunization

Various genera of the class Aves, such as chickens (Gallus domesticus), turkeys, and ducks, produce antibodies in blood and eggs against immunogens that cause avian diseases, as well as against other immunogens. For example, LeBacq-Verheyden et al. (Immunology 27:683 (1974)) and Leslie, G. A., et al. (J. Med. 130:1337 (1969)), have quantitatively analyzed immunoglobulins of the chicken. Polson, A., et al. (Immunological Communications 9:495–514 (1980)) immunized hens against several proteins and natural mixtures of proteins, and detected IgY antibodies in the yolks of the eggs. Fertel, R., et al. (Biochemical and Biophysical Research Communications 102:1028–1033 (1981)) immunized hens against prostaglandins and detected antibodies in the egg yolk. Jensenius et al. (Journal of Immunological Methods 46:63–68 (1981)) provide a method of isolating egg yolk IgG for use in immunodiagnostics. Polson et al. (Immunological Communications 9:475–493 (1980)) describe antibodies isolated from the yolk of hens that were immunized with a variety of plant viruses.

U.S. Pat. No. 4,357,272 discloses the isolation of antibodies from the yolks of eggs derived from hyperimmunized hens. The hyperimmunization was elicited by repetitive injections of immunogens derived from plant viruses, human IgG, tetanus antitoxin, snake antivenins, and Serameba. U.S. Pat. No. 4,550,019 discloses the isolation from egg yolks of antibodies raised in the hen by hyperimmunization with immunogens having a molecular or particle weight of at least 30,000. The immunogens used to hyperimmunize the chickens were selected from among plant viruses, human immunoglobulins, tetanus toxin, and snake venoms.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

U.S. patent application Ser. No. 09/233,379 discloses the existence of an anti-inflammatory factor found in the egg of a hyperimmunized avian.

An immunized egg is an egg which comes from an avian which has been immunized with, for example, a specific antigen or mixture of antigens. A hyperimmunized egg is an egg which comes from an avian which has been brought to a specific state of immunization by means of, for example, periodic booster administrations of antigens. Hyperimmunized eggs, no matter the type of antigen their avian maker has been administered, have been found to have various beneficial factors, including, as mentioned above, the treatment of chronic gastrointestinal disorders, NSAID-induces gastrointestinal damage (see U.S. application Ser. No. 08/688,576) and anti-inflammatory effects due to the presence of an anti-inflammatory composition (see U.S. application Ser. No. 09/233,379).

Glucosamine

Glucosamine a chondroprotective agent which has been studies for its potential beneficial effects in osteoarthritis. Chondroprotective agents are those which, in addition to relieving symptoms, appear to aid in balancing synthesis and degradation of cartilage tissue. Glucosamine has been known to biologists for several decades as an endogenous aminomonosaccharide synthesized from glucose. Its importance in joint dysfunctions relates to its physiologic role in the synthesis of proteoglycans and glycosaminoglycans, which are cartilage components. Research over the past four decades suggests that glucosamine is effective in reducing the symptoms of joint dysfunction and is well-tolerated. Glucosamine significantly reduces pain and tenderness and improves mobility.

Researchers have proposed several mechanisms for glucosamine's putative benefits in joint health. In vitro studies have suggested that glucosamine affects cartilage metabolism. One such effect may be the stimulation of proteoglycan synthesis, as seen with SAMe. Another possibility is that glucosamine enhances gene expression of the chondrocyte. In addition, glucosamine may act as an anti-inflammatory agent, though the effect is 50 to 300 times lower than NSAIDs. However, the NSAID exert their anti-inflammatory effects via inhibition of the cyclooxygenase enzyme system and thereby interfering with prostaglandins, while glucosamine does not. The anti-inflammatory effect may be the result of stimulating proteoglycan synthesis, which would stabilize cell membranes. A recent in vitro study demonstrated that glucosamine increased chondrocyte adhesion to fibronectin, effectively reversing the abnormal reduction in adhesion which occurs in joint degeneration.

SUMMARY OF THE INVENTION

The invention is based on the inventors' discovery that there is anti-inflammatory activity when egg and egg products, and in partuicular, hyperimmune egg or egg products, are combined with glucosamine and administered to a subject animal in that such administration results in the reduction, and sometime even prevention of inflammation and inflammatory related disorders in that subject animal.

In particular, the invention is directed to a composition comprising glucosamine and an egg product.

The invention is also directed to a method for reducing inflammation in a subject, the method comprising administering to the subject an effective amount of glucosamine and an egg product.

The invention is further directed to a method for reducing serum fibrinogen levels the method comprising administering to the subject an effective amount of glucosamine and an egg product.

The invention further encompasses a method for reducing or preventing the onset of rheumatoid arthritis the method comprising administering to the subject an effective amount of glucosamine and an egg product.

The invention finally covers a method for reducing or preventing the onset of osteoarthritis the method comprising administering to the subject an effective amount of glucosamine and an egg product.

DESCRIPTION OF THE INVENTION

Figure 1:
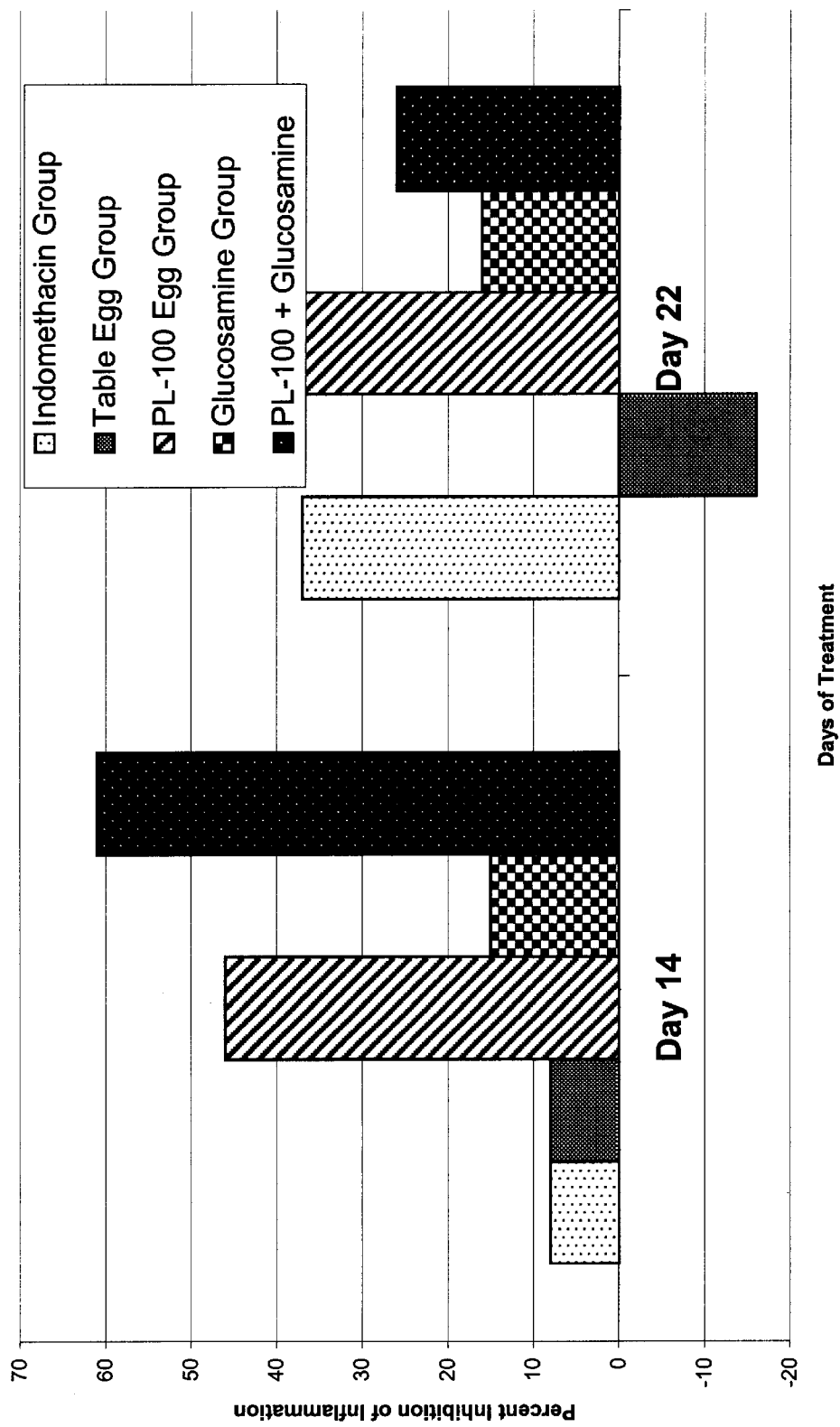
FIG. 1 is a bar graph depicting the effect of hyperimmune egg and glucosamine in the rat adjuvant arthritis model.

The invention relates to the discovery that the combination of egg-product with. glucosamine works synergistically against inflammation and inflammatory related disorders.

The following definitions apply throughout:

Definitions

The term "inflammation" is used in its art-recognized sense as a localized protective response elicited by injury or destruction of tissues which serves to destroy, dilute or wall off both the injurious agent and the injured tissue, characterized in the inappropriate, uncontrolled form by the classical sequence of pain, heat, redness, swelling, and loss of function, and histologically involving a complex series of events, including dilation of the arterioles, capillaries, and venules with increased permeability and blood flow, exudation of fluids including plasma proteins, and leukocyte migration into the inflammatory focus.

The term "arthritis" means any of a variety of disorders marked by inflammation and degeneration of connective tissue structures, especially the joints and related structures. It may be attended by pain, stiffness, or limitation of motion of these parts. Some forms of arthritis include rheumatoid arthritis, osteoarthritis, ankylosing seronegative spondyloarthropathy, reactive arthritis, chronic fatigue syndrome, fibromyalgia (fibrositis) and gout.

The term "autoimmune disease" is applied the standard medical definition as found in standard medical dictionaries such as Dorland's and Taber's. A description of a variety of autoimmune diseases can be found in the Background section of this document.

The term "hyperimmunization" means exposure to one or more antigens such that an immune response is elevated and maintained above the natural unexposed state.

The terms "egg" or "egg product" each means any whole egg (table, hyperimmunized or otherwise) or any product or fraction derived therefrom.

The terms "table egg" or "table egg product" each mean a whole egg, or any product or fraction derived therefrom, obtained from egg-producing animals which are not maintained in a hyperimmune state.

The terms "hyperimmune egg" or hyperimmune egg product" each mean whole egg or any product or fraction derived therefrom, obtained from an egg producing animal maintained in a hyperimmune state, and containing the anti-inflammatory composition as described in U.S. Ser. No. 09/233,379.

The term "supranormal levels" means levels in excess of those found in eggs of egg-producing animals not maintained in a hyperimmune state.

The term "anti-inflammatory composition" means the composition disclosed in U.S. Ser. No. 09/233,379 and herein, which counteracts or suppresses the inflammatory process.

The term "partially pure egg anti-inflammatory composition" means an anti-inflammatory composition described as such in U.S. Ser. No. 09/233,379.

The term "combinatorial derived immunogens" refers to a process of generating molecular diversity among immunogens by way of combinatorial synthesis.

The term "bioengineered immunogens" refers to immunogens which are obtained through the process of gene cloning technologies and genetic manipulation which allow the insertion and translation of proteins which have antigenic properties.

The term "genetic vaccine" refers to a nucleic acid vaccine which is generally produced by recombinant technologies and which may elicit an immune response.

The term "treatment" means that the onset of the symptoms (including pain) of the disorder and/or pathogenic origin of the disorder be delayed or completely prevented, or, if present, the symptoms be ameliorated or completely eliminated. For example, the hyperimmune egg plus glucosamine product treats arthritis and/or an autoimmune disease not only by suppressing the symptoms of the disorder in humans and other mammals, but also by acting as a prophylactic agent to counteract the presence of the disorder in the recipient.

The term "prevention" means that the progression of the disease is reduced and/or eliminated, or that the onset of the disease is eliminated.

The term "administer" means any method of providing a subject with a substance, including orally, intranasally, parenterally (intravenously, intramuscularly, or subcutaneously), rectally, topically or intraocularly.

The term "animal" means the animal kingdom definition.

The term "target animal" refers to an animal which functions as the egg or egg product producing animal.

The term "subject animal" refers to the animal which is administered the egg or egg product produced by the target animal.

The term "immunogen" means a substance that is able to induce a humoral antibody and/or cell-mediated immune response rather than immunological tolerance. The term signifies the ability to stimulate an immune response as well as react with the products of it, e.g., antibody.

The Invention

The present invention comprises a combination of hyperimmunized egg product and glucosamine. According to the principles of the invention, a combination of hyperimmunized egg product and glucosamine, in exogenous quantities, is provided to a subject experiencing an inflammatory reaction in order to reduce the inflammation.

In a preferred embodiment, the invention comprises a hyperimmune egg or egg product in combination with glucosamine which when administered to a subject animal is effective in reducing inflammation and in treating and preventing arthritis and/or an autoimmune disease in that subject animal. The hyperimmune egg is preferably obtained from an egg-producing animal, and more preferably, an avian, which has been hyperimmunized with at least one immunogen. The hyperimmune egg plus glucosamine product is one which is preferably administered orally to the subject animal. The hyperimmune egg or egg product and/or glucosamine can be further separated into more potent fractions which can subsequently be administered to a subject animal in a variety of forms. It is further contemplated that the Glucosamine and the egg product can be administered separately albeit preferably simultaneously. Glucosamine and table or hyperimmunized egg product work synergistically to reduce inflammation when administered in combination to a subject.

Glucosamine

The glucosamine provides the primary substrate for both collagen and proteoglycan synthesis. Administration of glucosamine to a subject bypasses the glucose to glucosamine rate-limiting step in the subject's natural production of collagen and proteoglycans because production of additional quantities of collagen and proteoglycans become available for use by the subject's natural healing processes to repair connective tissue.

The glucosamine is, preferably, in a salt form so as to facilitate its delivery and uptake by the subject. The preferred salt forms are glucosamine hydrochloride and glucosamine sulfate, among others. The use of the non-salt glucosamine is believed by many to fail to provide bioavailable glucosamine because the compound is not absorbed in the gastrointestinal tract. It is noted that in the case of the glucosamine sulfate, the sulfate may be available for later use in catalyzing the conversion of glucosamine to glycosaminoglycans. The unsulfated form is desired for the production of hyaluronic acid.

Regarding the administration of glucosamine, it is rapidly and almost completely absorbed into humans and other animals through oral administration and, as such, oral administration is most preferred. A significant portion of the ingested glucosamine localizes to cartilage and joint tissues, where it remains for long periods of time. This indicates that oral administration of glucosamine reaches connective tissues, where the glucosamine gets incorporated into newly-synthesized connective tissue.

Egg Product

The egg product is any egg or fraction of egg obtained from an egg-producing animal. In a preferred embodiment, the egg product of the invention is an egg obtained from an avian which has been manipulated, such as by hyperimmunization, to produce among other things supranormal levels of an anti-inflammatory composition in the egg (see U.S. application Ser. No. 09/233,379).

Hyperimmunization of the Egg-producing Animal

The hyperimmune egg or egg product can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of hyperimmune egg product.

When such egg-producing animals are brought to a specific state of immunization by means of, for example, periodic booster administrations of immunogens, the animals will produce eggs that, when consumed by a subject, will have beneficial properties, including supranormal levels of the anti-inflammatory composition, which when administered in combination with glucosamine are effective in the treatment and prevention of inflammatory related diseases as well as autoimmune diseases in that subject.

The induction of immune sensitivity alone is insufficient to cause the appearance of supranormal levels the egg anti-inflammatory composition in eggs, as is shown by the fact that table eggs do not contain these supranormal levels, even though the avians have been sensitized against various immunogens during normal immunization against avian diseases and during normal exposure to environmental factors. It is only in the specific hyperimmune states that the eggs have the desired supranormal levels of the anti-inflammatory composition.

This special state of hyperimmunization, in which the egg will become effective, in part because it will contain higher levels of the anti-inflammatory composition, is preferably achieved by administering an initial immunization, followed by periodic boosters with sufficiently high doses of specific immunogens or mixtures of immunogens. The preferred dosage of booster should be equal to or greater than 50% of the dosage necessary to produce primary immunization of the avian. Thus, there is a threshold booster dosage below which the properties are not produced in the avian's egg, even though the avian is in what normally would be called an immune state. Having knowledge of the requirement for developing and maintaining a hyperimmune state, it is within the skill of the art to vary the amount of immunogen administered, depending on the egg-producing animal genera and strain employed, in order to maintain the animal in the hyperimmune state.

The hyperimmune state is preferably produced by any immunogen or combination of immunogens. Hyperimmunization is preferably achieved by multiple exposures to multiple immunogens, multiple exposure to single immunogens, or single exposures to libraries of immunogens. Nearly any immunogen can be used to induce the hyperimmune state, including, but not limited to, bacterial, viral, protozoan, allergan, fungal or cellular substances.

Having knowledge of the requirement for developing and maintaining a hyperimmune state, it is within the skill of the art to vary the amount of immunogen administered, depending on the egg-producing animal genera and strain employed, in order to maintain the animal in the hyperimmune state.

In addition to immunizations with naturally occurring immunogens, immunization may also be accomplished using immunogens which are synthetically derived by combinatorial chemistries. The basic strategy is to assemble multiple combinations of chemical building blocks for producing a population of molecules with diversity. Several methods have recently been developed for solid and solution phase combinatorial synthesis of libraries of oligomers (Fodor, S. et al., Science 251:767 (1991); Houghton, R. et al., Nature 354:82 (1991)) as well as small organic molecules (Bunin, B. & Ellman, J., J. Am. Chem. Soc. 114:10997 (1992)). Rapid multiple peptide and oligomer synthesis can serve as a source for combinatorial derived immunogens. Furthermore, an alternative strategy would allow the addition of organic building blocks in combinatorial fashion to a backbone molecule for improved immunogenicity.

Alternative modes of hyperimmunizing egg producing animals can be used in place of immunogenic vaccines and include the use of genetic vaccines. In particular, any DNA construct (generally consisting of a promoter region and an antigen encoding sequence) will trigger an immune response. Genetic vaccines consist of antigen-coding vectors, fragments of naked DNA, plasmid DNA, DNA-RNA antigens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities may be necessary and generally result in more persistent immunogen production. When using such genetic processes, the preferred method for introducing DNA into avians is through intramuscular injection of the DNA into the breast muscle.

Methods of DNA delivery include, but are not limited to, particle bombardment, direct injection, liposomes, jet injection (Fynan, E. F. et al., Proc. Natl. Acad. Sci. USA 90:11478–11482 (1993)). The nucleic acids that code for known or unknown immunogens, promoter regions (notably CMV cauliflower mosaic virus) and SV40 bacterial origin can be replicated in bacteria to produce plasmid DNA for use in DNA injections. Although several routes of parenteral administration of the DNA are effective in chickens, the preferred method is intramuscular injection to the breast muscle. Vaccine trials are carried out in egg laying avians, preferably chickens. Repeated immunizations are given at one to two week intervals for up to six months.

It is preferred that the amounts of DNA used are generally in the order of 50–300 µg of DNA in saline for direct injection. For particle bombardment, 4–100 µg of DNA co-precipitated onto gold beads by the addition of 2.5 M $CaCl_2$ are preferred. Repeated immunizations can be given intradermally by this method of accelerating DNA coated particles into the live animal.

The following is a detailed description of a preferred procedure used to bring an egg-producing animal to a heightened state of immunity from which the resultant hyperimmunized egg or egg product can be administered to a subject:

1. Selecting one or more immunogens.
2. Eliciting an immune response in the egg-producing animal by primary immunization.
3. Administering booster vaccines of immunogens of appropriate dosage to induce and maintain the hyperimmune state.
4. Testing the hyperimmune eggs for anti-inflammatory activity levels.
5. Collecting and processing the eggs.

Below is a more detailed description of this procedure.

Step 1: Any immunogen or combination of immunogens may be employed as a vaccine. The immunogens can be bacterial, viral, protozoan, fungal, cellular, or any other substances to which the immune system of an egg-producing animal will respond. The critical point in this step is that the immunogen(s) must be capable of inducing immune and hyperimmune states in the egg-producing animal. Although only a single immunogen may function as the vaccine for the method of the invention, one preferred vaccine is a mixture of polyvalent bacterial and viral antigens selected from the following antigen families: the enteric bacilli and bacteroides, pneumococci, pseudomonas, salmonella, streptococci, bacilli, staphylococci, neisseria, clostridia, mycobacteria, actinomycetes chlamydiae, and mycoplasma. Viral antigens are preferably selected from the following antigen families: adenoviruses, picornaviruses and herpes viruses, although other viral antigen families will work.

In a preferred embodiment, a polyvalent vaccine referred to as PL-100 is used. The bacteria included in the PL-100 vaccine are listed in Table 1 of Example 1. This vaccine has been previously described in U.S. Pat. No. 5,772,999 and U.S. patent application Ser. No. 09/233,379 both assigned to DCV, Inc.

Step 2: The vaccine can be either a killed or live-attenuated vaccine and can be administered by any method that elicits an immune response. It is preferred that immunization be accomplished by administering the immunogens through intramuscular injection. The preferred muscle for injection in an avian is the breast muscle. Dosage is preferably 0.05–5 milligrams of the immunogenic vaccine. Other methods of administration that can be used include intravenous injection, intraperitoneal injection, intradermal, rectal suppository, aerosal, oral, topical or ocular administration. When DNA techniques are used for the hyperimmunization process, much smaller quantities are required, generally 300 micrograms.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of antigen necessary to induce an immune response depends on the vaccination procedure used, including the type of adjuvants and formulation of antigen(s) used as well as the type of egg-producing animal used as the host.

Step 3: The hyperimmune state is preferably induced and maintained in the target animal by repeated booster administrations of an appropriate dosage at fixed time intervals. The time intervals are preferably 2–8 week intervals over a period of 6–12 months. However, it is essential that the booster administrations do not lead to immune tolerance. Such processes are well known in the art.

It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means.

Several combinations of primary and hyperimmunization are known to those skilled in the art.

Step 4. It is appropriate to test the eggs for anti-inflammatory activity levels. This can be accomplished by any clinical and pre-clinical evaluation that tests the effects of either the hyperimmune egg, or products derived therefrom, on inflammation.

Step 5. This step involves the collection and processing of the hyperimmunized egg(s). The egg can be collected by conventional methods. Processing the egg can be accomplished in a variety of ways described later in this document. The egg can also be further processed to purify anti-inflammatory compositions as described in U.S. Ser. No. 09/233,379.

Processing And Administration

It is preferred that the eggs or fractions thereof, including the partially purified anti-inflammatory composition, collected from hyperimmunized animals are processed to produce a hyperimmune egg product, which can subsequently be administered to a subject animal in combination with glucosamine to treat an inflammatory disorder.

The egg itself or fractions thereof, including the partially purified anti-inflammatory composition of the present invention, are administered to a subject animal in combination with glucosamine by any means that treats or prevents inflammation, including arthritis, and/or autoimmune disease in the subject animal. It is preferred that administration occur by directly feeding the egg or any derivative of the egg in combination with glucosamine to the subject animal. It is important to note that whole egg, egg yolk, and egg white are natural food ingredients which are non-toxic and safe.

In an alternative embodiment, glucosamine and the egg or any fraction thereof, including the partially purified anti-inflammatory composition, are integrated into a nutritional supplement. With particular regard to the egg, one preferred method for preparing the egg or any fraction thereof to be incorporated into a nutritional supplement involves drying the egg into an egg powder. Although various methods are known for drying eggs, spray drying is a preferred method. The process of spray drying eggs is well known in the art.

Such a dried egg powder can be incorporated into drinks in the form of, for example, protein powders, power building drinks, protein supplements and any other nutritional, athlete-associated products. In addition, the egg powder can be used in bake mixes, power bars, candies, cookies, etc. Other examples of egg processing include making an omelet, soft or hard-boiling the egg, baking the egg, or, if desired, the egg can be eaten raw or processed as liquid egg.

The inventors submit that the glucosamine and egg, although preferably administered in combination, do not need to be administered in the same form or in one product. For instance, the glucosamine could be taken in pill form while the egg product is administered as a drink.

Should one prefer to combine the partially pure anti-inflammatory composition with glucosamine, then the egg can even be further separated to purify the partially purified anti-inflammatory composition, as described earlier which will allow for other modes of administration such as separately administering egg product parenterally, subcutaneously, intravenously, intramuscularly, intraperitoneally, intranasally, orally or topically. In addition, such further separation will provide for the ability to make encapsulated products and pharmaceutical compositions with said egg or fraction thereof.

Preparations of the anti-inflammatory composition for parenteral administration include sterile aqueous or non-aqueous solutions, suspensions or emulsions. Examples of nonaqueous solvents or vehicles are propylene glycol, polyethylene glycol, vegetable oils such as olive oil and injectable organic esters such as ethyl oleate.

With particular reference to the partially pure anti-inflammatory composition, oral administration is preferably accomplished through solid dosage forms which include capsules, tablets, pills, powders and granules, among others. In solid dosage forms, the anti-inflammatory composition is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents, pH sensitive polymers, or any other slow-releasing encapsulants which are typically used as encapsulating compositions in the food and drug industry. Tablets and pills can additionally be prepared with an enteric coating.

Liquid dosage forms of the anti-inflammatory composition for oral administration include pharmaceutically acceptable emulsions, solutions, suspensions, syrups and elixirs, containing inert diluents commonly used in the pharmaceutical art. Besides inert diluents, compositions can also include wetting agents, emulsifying, and suspending, and sweetening agents.

Combination of Glucosamine and Immunized Egg Product

Glucosamine and egg product, as described above, work synergistically, when administered concurrently to a subject, to reduce inflammation in that subject.

With regard to the administration of both glucosamine and immunized egg product, in one embodiment, an effective amount of glucosamine is administered to the subject independently of an effective amount of immunized egg product. In an alternate embodiment, the subject is administered a composition comprising an effective amount of glucosamine and immunized egg product. Either method of administration will effectuate a synergistic effect.

The administration to the subject should be carried out in an amount that is effective for treating or preventing inflammation. It is preferred that the subject is administered a higher dosage of glucosamine mixed with a lower dosage of immunized egg product. Depending on the particular disorder it may be more preferred vice versa, then such unequal dosages are appropriate for treatment and prevention, and should be administered in those amounts. Due to the synergistic effect of these two compositions, administration may need to be adjusted accordingly. Those having skill in the art are familiar with determining dosage amounts that will best treat and prevent inflammation of interest.

The glucosamine and egg of the present invention may be administered by any means that provide anti-inflammatory activity. For example, administration may be parenteral, subcutaneous, intravenous, intramuscular, intraperitoneal, intranasal, or oral.

Oral administration is preferably accomplished through solid dosage forms which include capsules, tablets, pills, powders and granules, among others. In solid dosage forms, the glucosamine and egg product are admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents, pH sensitive polymers, or any other slow-releasing encapsulants which are typically used as encapsulating compositions in the food and drug industry. Tablets and pills can additionally be prepared with an enteric coating.

Liquid dosage forms of the glucosamine and egg product combination for oral administration include pharmaceutically acceptable emulsions, solutions, suspensions, syrups and elixirs, containing inert diluents commonly used in the pharmaceutical art. Besides inert diluents, compositions can also include wetting agents, emulsifying, and suspending, and sweetening agents.

Preparations of the glucosamine and egg product combination for parenteral administration include sterile aqueous or nonaqueous solutions, suspensions or emulsions. Examples of nonaqueous solvents or vehicles are propylene glycol, polyethylene glycol, vegetable oils such as olive oil and injectable organic esters such as ethyl oleate.

The dosage of active ingredients may be varied; however it is necessary that the amount of the active ingredient shall be such that a suitable dosage form is obtained. It will be recognized that the selected dosage form depends upon the desired therapeutic effect, on the route of the administration and on the duration of the treatment.

Administration dosage and frequency will depend on the age and general health condition of the patient, taking into consideration the possibility of side effects. Administration will also be dependent on concurrent treatment with other drugs and patients' tolerance of the administered drug.

With regard to administration to a subject of the hyperimmunized egg or egg product, it has been determined, and is detailed in the following examples, that the preferred dose range of hyperimmunized egg or egg product to be given to a subject is between 100 milligrams to 10 grams per kilogram of subject weight.

With regard to the partially purified anti-inflammatory composition itself, it has been determined that the preferred dose range of the partially purified composition, purified and isolated from whole egg, egg yolk and egg white of a hyperimmunized egg, is between 1 microgram and 400 milligrams per kilogram of the anti-inflammatory composition.

With regard to administration to a subject of the glucosamine, it has been determined, and is detailed in the following examples, that the preferred dose range of glucosamine to be given to a subject is between 10 milligrams to 5 grams per kilogram of subject weight. And more preferably, 100 milligrams to 2.5 grams of subject weight.

In a preferred embodiment, a 50 lb subject suffering from inflammation should be administered a single tablet, twice a day, comprising 250 mg of glucosamine HCl, 750 mg of hyperimmunized egg product and 320 mg of coated ester C. The administration is continued as long as needed to reduce or prevent inflammation. Duration and intensity of the treatment will depend on the particular condition and the advancement of the subject's condition.

Examples of inflammatory conditions that may be treated by administration of the glucosamine and egg product of the present invention include all forms of arthritis, including, but not limited to, rheumatoid arthritis, osteoarthritis, ankylosing seronegative spondyloarthropathy, reactive arthritis, chronic fatigue syndrome, fibromyalgia (fibrositis) and gout. The egg product of the invention is equally effective in treating autoimmune diseases, such as rheumatoid arthritis, juvenile diabetes, multiple sclerosis, Graves' disease, Meneri's disease, myasthenia gravis, lupus erythematosus, psoriasis, systemic scleroderma, rheumatic fever, Sjogren syndrome among others; acute and subacute bursitis, acute non-specific tendonitis, systemic lupus erythematosus, systemic dermatomyositis, acute rheumatic carditis, pemphigus, bullous dermatitis, herpeteformis, severe erythemna, multiform exfoliative dermatitis, cirrhosis, seasonal perennial rhinitis, bronchial asthma, ectopic dermatitis, serum sickness, keratitis, opthalmicus iritis, diffuse ureitis, chorditis, optic neuritis, sympathetic ophthalmia, symptomatic sarcoidosis, Loeffler's syndrome, berylliosis, hemolytic anemia, mastitis, mastoiditis, contact dermatitis, allergic conjunctivitis, psoriatic arthritis, ankylosing spondylitis, acute gouty arthritis, herpes zoster rheumatoid arthritis, osteoarthritis, any other degenerative joint diseases, and any other related autoimmune diseases. Further, the glucosamine and egg product combination may be used to treat individuals who are exposed to potentially inflammatory agents such as allergens.

When it comes to treatment and prevention of a particular disorder, whether it be inflammation in general or a form of arthritis or an autoimmune disease, Glucosamine in combination with the hyperimmune egg product or any active fraction thereof, including the partially purified anti-inflammatory composition, is preferably administered to the subject in an amount that is immunologically effective in treating and preventing the particular disorder. Duration and intensity of the treatment will depend upon the particular condition, whether it is present, and, if so, the advancement of the condition in the subject. Glucosamine in combination with the hyperimmune egg product or any active fraction thereof, including the partially purified anti-inflammatory composition, are also provided in any amount that treats and/or prevents the condition and the symptoms of the condition. For example, in some cases, daily amounts ranging from less than one to several whole, hyperimmune eggs (or hyperimmune egg products containing the equivalent of less than one to several whole, hyperimmune eggs) can be administered in combination with an effective dose of glucosamine to the subject depending on the particular circumstance of the condition. More potent fractions can be separated and concentrated by methods described herein as well as other known methods in the art.

The dosage of active ingredients may be varied; however it is necessary that the amount of the active ingredient shall be such that a suitable dosage form is obtained. It will be recognized that the selected dosage form depends upon the desired therapeutic effect, on the route of the administration and on the duration of the treatment.

The advantageous properties of this invention can be observed by reference to the following examples which illustrate the invention.

EXAMPLES

Example 1

Preparation of PL-100 Vaccine

A bacterial culture containing the spectrum of bacteria shown in Table 1 below, as obtained from the American Type Culture Collection, was reconstituted with 15 mL of media and incubated overnight at 37 C. Once good growth was obtained, approximately one-half of the bacterial suspension was employed to inoculate one liter of broth with the inoculate being incubated at 37 C.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet was resuspended in a small amount of double distilled water.

The media-free bacterial suspension was killed by placing the suspension in a glass flask in an 80 C. water bath overnight. The viability if the broth culture was tested with a small amount of killed bacteria, incubated at 37 C. for five days and checked daily for growth to certify that the bacteria had been killed.

The killed bacteria were lyophilized until dry. The dry bacteria were then mixed with sterile saline solution to a concentration of $2.2 \times 10^8$ bacterial cells/mL saline (1.0 optical density reading at 660 nm). Bacteria contained in PL-100 vaccine are listed in Table 1 below.

TABLE 1

| PL-100 Bacterial List | |
|---|---|
| Escherichia coli | Escherichia coli (Aerobacter) |
| Klebsiella pneumoniae | Pseudomonas aeruginosa |
| Salmonella typhimurium | Shigella dysenteriae |
| Salmonella enteriditis | Staphylococcus epidermis |
| Staphylococcus simulans | Streptococcus pyogenes, type 1 |
| Streptococcus pyogenes, type 3 | Streptococcus pyogenes, type 5 |
| Streptococcus pyogenes, type 8 | Streptococcus pyogenes, type 12 |
| Streptococcus pyogenes, type 14 | Streptococcus pyogenes, type 18 |
| Streptococcus pyogenes, type 22 | Proteus vulgaris |
| Streptococcus agalactiae | Streptococcus mitis |
| Streptococcus mutans | Streptococcus salavarius |
| Streptococcus sanguis | Streptococcus pneumoniae |
| Propionibacterium acnes | Haemophilis influenzae |

Immunization Procedure for Hyperimmunized Egg Product

A killed preparation of pathogens was prepared as described above. For the first vaccination, the bacteria were mixed with complete Freund's adjuvant, and 5.6 mg of bacterial material was injected into the breast muscle of a chicken. For the remaining vaccines, the bacterial preparation was mixed with incomplete Freund's adjuvant and injected into the chickens at two week intervals for six months.

Example 2

Objective

To assess the synergistic antiarthritic effect of Glucosamine hydrochloride and the DCV hyperimmune egg in the established rat adjuvant arthritis, a chronic animal model of inflammation.

Results

Table 1 shows all the paw edema data on days 14, 22 and 30 of the study. The results indicate that the PL-100+ Glucosamine HCl group showed the highest percent inhibition of inflammation on days 14 and 30 of the disease. The PL-100 egg and Glucosamine hydrochloride by itself showed inhibitory effect on days 14 and 22 of the study, while they both showed ineffectiveness on day 30 when the disease has rapidly progressed to a severe polyarthritis.

Table 2 shows all the serum fibrinogen levels on days 16, 23 and 30 of the study. The results indicate that the Fibrinogen levels initially increase on day 16 followed by a drop in levels on day 23 and 30. However, the increase in levels on day 16 is least in PL-100+Glucosamine HCl group as compared to PL-100 and Glucosamine HCl alone, and also the inhibition of serum fibrinogen levels is highest in PL-100+Glucosamine HCl group as compared to the PL-100 and Glucosamine HCl groups individually. Also, on day 30, the percent inhibition of fibrinogen levels in the PL-100+ Glucosamine HCl group is 32% as compared to 46% in the Indomethacin treated group.

Table 3 shows all the Histomorphologic observations on day 22 and 30 of the study. The results show that the inflammation of periarticular/soft tissue, (which indicates the infiltration of mononuclear and/or polymorphonuclear inflammatory cells into the soft tissues, including synovial membranes around the joint) is least affected in the PL-100+Glucosamine group both on day 22 and 30 as compared to the other groups.

The Hyperostosis condition, (which indicates increased and excessive amounts of new bone growth, particularly in subperiosteal areas) is least in the PL-100+Glucosamine HCl group on day 22 and low on day 30 as compared to the other groups.

The cartilage erosion on day 22 and 30 is least in the PL-100+Glucosamine HCl group as compared to the other groups.

The pannus cartilage, (an accumulation of inflammatory cells, exudate, fibrin or fibrous tissues on joint surfaces) is least affected on day 22 and 30 in the PL-100+Glucosamine HCl treated group as compared with the other groups.

The Ankylosis, (which denotes enlarged and immobile joints due to the formation of fibrous and inflammatory tissues between joint surfaces, usually with complete loss of cartilage and replacement in this area with fibrous tissue that results in adhesions and joint cavities) is minimal in the PL-100+Glucosamine HCl group as compared with any other group.

Finally, the osteolysis, (which indicates the necrosis and lysis of the bone) is absent in PL-100+Glucosamine HCl treated group on day 22 as compared to the other groups, where there is some degree of lysis present.

TABLE 1

DCV Rat Adjuvant
Effect of Immune Egg Preparations, Glucosamine, singly and in combinations, and CAF in the Rat Established Adjuvant Arthritis Model

| GP | Oral[a] Treatment | Day 14-Mean Paw Edeman (ml ± SE), n | % Chg | Day 22-Mean Paw Edema (ml ± SE), n | % Chg | Day 30-Mean Paw Edema (ml ± SE), n | % Chg |
|---|---|---|---|---|---|---|---|
| 1 | PL-200 + GLU-250 | 1.5 ± 0.2, n = 8 | +15 | 1.7 ± 0.1, n = 7 | −26 | 2.4 ± 0.3, n = 5 | +14 |
| 2 | PL-100 | 0.7 ± 0.3, n = 5 | −46 | 1.2 ± 0.2, n = 5 | −37 | 2.5 ± 0.3, n = 5 | +19 |
| 3 | PL-100 + GLU-250 | 0.5 ± 0.3, n = 6 | −61 | 1.4 ± 0.2, n = 6 | −26 | 1.8 ± 0.2, n = 6 | −14 |
| 4 | GLU-250 | 1.1 ± 0.3, n = 7 | −15 | 1.6 ± 0.3, n = 7 | −16 | 3.1 ± 0.2, n = 5 | +48* |
| 5 | CAF | 0.8 ± 0.2, n = 5 | −38 | 1.8 ± 0.3, n = 5 | − 5 | 2.3, n = 2 | +10 |
| 6 | Whole Egg | 1.2 ± 0.4, n = 5 | −8 | 2.2 ± 0.5, n = 5 | 16 | 1.9 ± 0.2, n = 5 | −10 |
| 7 | Indo - 1 mg/kg | 1.2 ± 0.4, n = 6 | −8 | 1.2 ± 0.1, n = 6 | −37 | 0.3 ± 0.1, n = 5 | −86* |
| 8 | Control Adjuvant | 1.3 ± 0.3, n = 8 | — | 1.9 ± 0.2, n = 8 | — | 2.1 ± 0.2, n = 6 | — |
| 9 | Normal | 0[b], n = 3 | — | 0.2, n = 3 | — | 0.3, n = 2 | — |

[a]Test articles were given in 1 mL of deionized water, when not in a combination an extra 1 mL of water was given to each rat
[b]Normal paw growth
*P ≤ 0.05 from Control Adjuvant (Dunnett's Test)

TABLE 2

Effects of Immune Egg Preparations, Glucosamine, Singly And In Combinations with PL-100 and Chondroitin $SO_4$, And CAF in the Rat Established Adjuvant Arthritis Model
Mean Plasma Fibrinogen Levels (mg/dl ± SE)

| GP | Treatment | Oral Dose | n | Day 16 | % Δ from ctrl | Day 23 | % Δ from ctrl | Day 30 | % Δ from ctrl |
|---|---|---|---|---|---|---|---|---|---|
| 1 | PL 100 | 2 ml | 5 | 841 ± 34 | +35 | 707 ± 70 | −14 | 550 ± 89 | −19 |
| 2 | Gluco HCl | 2 ml | 5 | 735 ± 44 | +18 | 803 ± 39 | −2 | 487 ± 112 | −28 |
| 3 | Gluco HCl + PL 100 | 2 ml | 5 | 735 ± 29 | +7 | 710 ± 37 | −14 | 457 ± 42 | −32 |
| 4 | CAF | 2 ml | 5 | 788 ± 57 | +26 | 776 ± 58 | −6 | 560 ± 59 | −17 |
| 5 | Gluco HCl + Chond $SO_4$ | 2 ml | 5 | 658 ± 84 | +5 | 701 ± 51 | −15 | 574 ± 109 | −15 |
| 6 | Indomethacin | 4 mg/kg | 5 | 590 ± 86[a] (n = 4)[b] | — | 617 ± 72 | −28 | 366 ± 48 | −46* |
| 7 | Control Adjuvant | 2 ml | 5 | 625 ± 73 | — | 822 ± 40 | — | 672 ± 72 | — |
| 8 | Normal | — | 5 | 186 ± 5 | — | 178 ± 4 | — | 193 ± 9 | — |

[a]Control fibrinogen levels since indomethacin was not dosed until Day 16.
[b]One of the plasma samples clotted
*p ≤ 0.05 Dunnett's test

TABLE 3

Incidence Of Histomorphologic Observations

|  | Control Day 22/30 | Indomethacin Day 22/30 | Glucosamine Day 22/30 | Table Egg Day 22/30 | PL-100 Egg Day 22/30 | PL 100 Egg & Glucosamine Day 22/30 |
|---|---|---|---|---|---|---|
| Tibiotarsal Joint (H&E) | | | | | | |
| Inflammation, periarticular | 3.5/3.5 | 3.5/3.5 | 3.5/4.0 | 2.5/4.0 | 2/3.5 | 1.0/3.0 |
| Hyperostosis | 3.0/2.5 | 3.0/2.0 | 3.0/3.5 | 1.0/2.0 | 0.5/3.0 | 0.0/2.5 |
| Erosion, Cartliage | 3.0/2.0 | 1.5/2.5 | 2.0/4.0 | 1.5/2.5 | 1.0/3.0 | 0.0/1.0 |
| Pannus, Cartliage | 3.0/3.0 | 1.5/2.5 | 2.0/4.0 | 1.5/2.5 | 1.0/3.0 | 0.0/1.0 |
| Ankylosis | 2.0/3.0 | 1.5/1.5 | 3.5/4.0 | 1.5/2.0 | 1.0/3.0 | 0.0/1.5 |
| Osteolysis | 2.5/1.0 | 2.5/1.0 | 1.5/3.5 | 1.0/2.0 | 0.0/3.0 | 0.0/2.5 |
| Tibiotarsal Joint (PAS) | | | | | | |
| Erosion, Cartilage | 3.0/3.0 | 1.5/2.5 | 2.0/4.0 | 1.5/2.5 | 1.0/3.0 | 0.0/1.0 |

Figure 2:
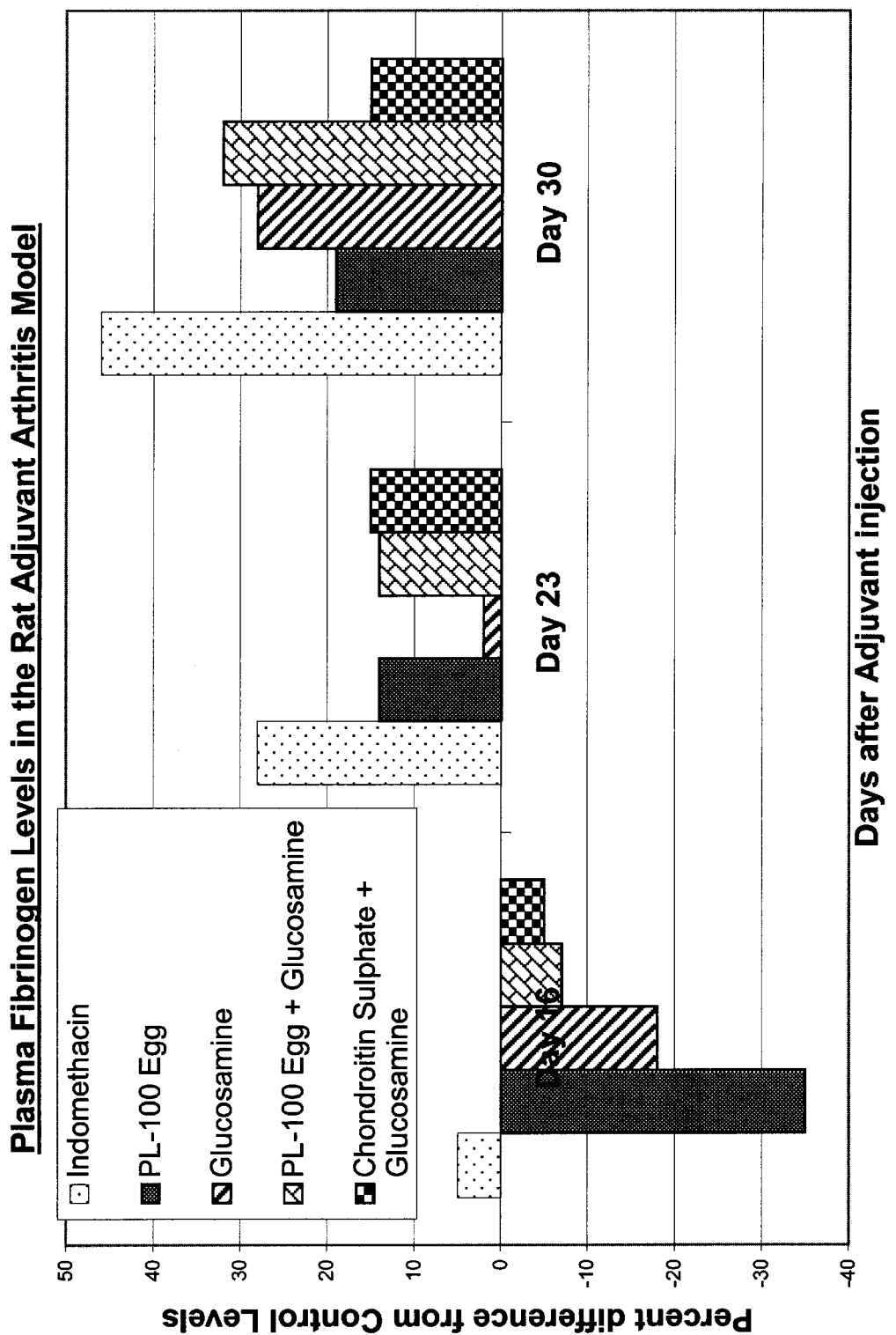
FIG. 2 is a bar graph depicting plasma fibrinogen levels in the rat adjuvant arthritis model.

Key:
0  Within normal limits
1  Minimal degree or amount of indicated change
2  Mild degree or amount of indicated change
3  Moderate degree or amount of indicated change
4  Severe degree or amount of indicated change Summary In the rat adjuvant arthritis model, which is a chronic animal model for inflammation, the PL-100 egg and Glucosamine HCl showed an additive effect in a) reducing the left hind paw swelling of the animal, thereby showing anti-inflammatory effect on days 14, 22 and 30,
b) reducing the serum fibrinogen levels (which is an accepted serum marker for inflammation) after day 22 of injection, and continued till day 30, which was the end of the study,
c) minimizes the effect on the periarticular/soft tissues from the infiltration of mononuclear and polymorphonuclear cells on day 22, when the intensity of rheumatoid arthritis is at its peak
d) completely protects from hyperostosis on day 22 of the study,
e) completely protects the erosion of the cartilage around the arthritic joints, on day 22 and minimizes the damage on day 30,
f) completely protects the cartilage in the pannus area on day 22, and minimizes the damage on day 30,
g) completely protects the affected joints from ankylosis on day 22, completely protects bones in the arthritic joint area from osteolysis on day 22.
h) FIG. 1 shows all the paw edema data on days 14, 22 of the study. The results indicate that the PL-100+ Glucosamine HCl group showed the highest percent inhibition of inflammation on day 14 of the disease.
i) FIG. 2 shows all the serum fibrinogen levels on days 16, 23 and 30 of the study. The results indicate that the Fibrinogen levels initially increase on day 16 followed by a drop in levels on day 23 and 30. However, the increase in levels on day 16 is least in PL-100+ Glucosamine HCl group as compared to PL-100 and Glucosamine HCl alone, and also the inhibition of serum fibrinogen levels is highest in PL-100+ Glucosamine HCl group as compared to the PL-100 and Glucosamine HCl groups individually. Also, on day 30, the percent inhibition of fibrinogen levels in the PL-100+Glucosamine HCl group is 32% as compared to 46% in the Indomethacin treated group. Thus PL-100+Glucosamine HCl not only restricts the severity of inflammation at the beginning of the disease, but also inhibits it towards the end of the study (as indicated by the serum inflammatory marker levels).

We claim:

1. A composition comprising glucosamine and whole egg wherein the whole egg is obtained from an egg-producing animal that has been hyperimmunized with an immunogenic vaccine, said immunogenic vaccine comprising antigens selected from the group consisting of bacterial, viral, protozoan, fungal and cellular immunogens and mixtures thereof.

2. The composition of claim 1 wherein the glucosamine is selected from the group consisting of glucosamine HCl and glucosamine sulfate.

3. The composition of claim 1 wherein the whole egg further comprises an anti-inflammatory composition.

4. The composition of claim 1 wherein the amount of whole egg comprises between approximately 100 milligrams and 10 grams of whole egg per kilogram of weight of a subject to which said composition is administered.

5. The composition of claim 1 wherein the amount of glucosamine comprises between approximately 10 milligrams and 5 grams.

6. The composition of claim 1 wherein the immunogenic vaccine comprises immunogens selected from the group consisting of: *Escherichia coli, Escherichia coli* (Aerobacter), *Klebsiella pneumoniae, Pseudomonas aeruginosa, Salmonella typhimurium, Shigella dysenteriae, Salmonella enteriditis, Staphylococcus epidermis, Staphylococcus simulans, Streptococcus pyogenes*, type 1, *Streptococcus pyogenes*, type 3, *Streptococcus pyogenes*, type 5, *Streptococcus pyogenes*, type 8, *Streptococcus pyogenes*, type 12, *Streptococcus pyogenes, type 14, Streptococcus pyogenes*, type 18, *Streptococcus pyogenes*, type 22, *Proteus vulgaris, Streptococcus agalactiae, Streptococcus mitis, Streptococcus mutans, Streptococcus salavarius, Strepto-*

*coccus sanguis, Streptococcus pneumoniae, Propionibacterium acnes* and *Haemophilis influenzae.*

7. A method for reducing serum fibrinogen levels in a subject, the method comprising administering to the subject an effective amount of a composition comprising glucosamine and whole egg wherein the whole egg is obtained from an egg-producing animal which has been hyperimmunized with an immunogenic vaccine, said immunogenic vaccine comprising antigens selected from the group consisting of bacterial, viral, protozoan, fungal and cellular immunogens and mixtures thereof.

8. The method of claim 7 wherein the effective amount of whole egg comprises between approximately 100 milligrams and 10 grams of whole egg per kilogram of weight of a subject to which said composition is administered.

9. The method of claim 7 wherein the effective amount of glucosamine comprises between approximately 10 milligrams and 5 grams.

10. The method of claim 7 wherein the composition is administered by a method selected from the group consisting of parenterally, subcutaneously, intravenously, intramuscularly, intraperitoneally, intranasally, orally and topically.

11. The method of claim 7 wherein the whole egg is dried to form a dried egg powder.

12. The method of claim 1 wherein the whole egg is dried to form a dried egg powder.

* * * * *